United States Patent
Ethell

(10) Patent No.: US 9,789,292 B2
(45) Date of Patent: Oct. 17, 2017

(54) METHOD AND USE OF DRAINING FLUID ABOVE THE CRIBRIFORM PLATE

(71) Applicant: Douglas Wayne Ethell, Riverside, CA (US)

(72) Inventor: Douglas Wayne Ethell, Riverside, CA (US)

(*) Notice: Subject to any disclaimer, the term of this patent is extended or adjusted under 35 U.S.C. 154(b) by 223 days.

(21) Appl. No.: 14/692,996

(22) Filed: Apr. 22, 2015

(65) Prior Publication Data

US 2016/0310713 A1    Oct. 27, 2016

Related U.S. Application Data

(60) Provisional application No. 61/983,317, filed on Apr. 23, 2014.

(51) Int. Cl.
- *A61M 5/00* (2006.01)
- *A61M 27/00* (2006.01)

(52) U.S. Cl.
CPC ................. *A61M 27/006* (2013.01)

(58) Field of Classification Search
CPC .................................................. A61M 27/006
See application file for complete search history.

(56) References Cited

U.S. PATENT DOCUMENTS

| | | | | |
|---|---|---|---|---|
| 7,906,643 B2* | 3/2011 | DiMauro | ............. | C07D 279/28 544/37 |
| 8,945,600 B2* | 2/2015 | Bleier | ................. | A61K 31/137 424/422 |
| 2012/0259265 A1* | 10/2012 | Salehi | ................. | A61M 1/0021 604/9 |

OTHER PUBLICATIONS

Ethell, DW "Disruption of Cerebrospinal Fluid Flow through the Olfactory System May Contribute to Alzheimer's Disease Pathogenesis." Journal of Alzheimer's Disease 41 (2014) 1021-1030.*

Photo of Journal with display/available to public date.*

* cited by examiner

Primary Examiner — Leslie Deak
(74) Attorney, Agent, or Firm — Mintz Levin Cohn Ferris Glovsky and Popeo, P.C.

(57) ABSTRACT

Alzheimer's disease is a neurological disorder marked by progressive memory and cognitive impairments that eventually result in death. Currently, there are no effective therapies or cures that slow or halt the relentless progression of Alzheimer's disease. The invention teaches that the underlying mechanism responsible for the initiation of Alzheimer's disease is due to the insufficient flow of cerebrospinal fluid through apertures in the cribriform plate. The cribriform plate is a flat bony structure at the top of the nasal cavity directly below the olfactory bulbs. Naturally occurring apertures in the cribriform plate provide conduits for cranial nerve 1 fibers passing from the olfactory epithelium below, into the olfactory bulb above. Cerebrospinal fluid in the extracellular compartment above seeps through these apertures and into the nasal submucosa below, where it is removed by lymphatic vessels. This outflow allows cerebrospinal fluid to flow into the olfactory bulbs from contiguous brain structures that include the basal forebrain and medial temporal lobe. Cerebrospinal fluid flow along this route removes metabolites and debris from those regions of the brain, including factors that accumulate in the early stages of Alzheimer's disease. Obstructions of cribriform plate apertures reduce or stop this outflow of cerebrospinal fluid, resulting in the accumulation of plaques and tangles and other Alzheimer's disease related pathologies. The invention teaches that patients with Alzheimer's disease and other forms of dementia can be treated by inserting shunts that facilitate the outflow of cerebrospinal fluid from an area above the cribriform plate to other parts of the body including but not limited to other regions of the brain, the nasal submucosa, the peritoneal cavity, and the pleural cavity. It provides a method of treating any patient in need thereof for neurological or psychiatric disease. The invention teaches how shunts can be configured and implanted with two independent claims and five dependent claims.

3 Claims, 3 Drawing Sheets

Insertion of a cribriform plate shunt.

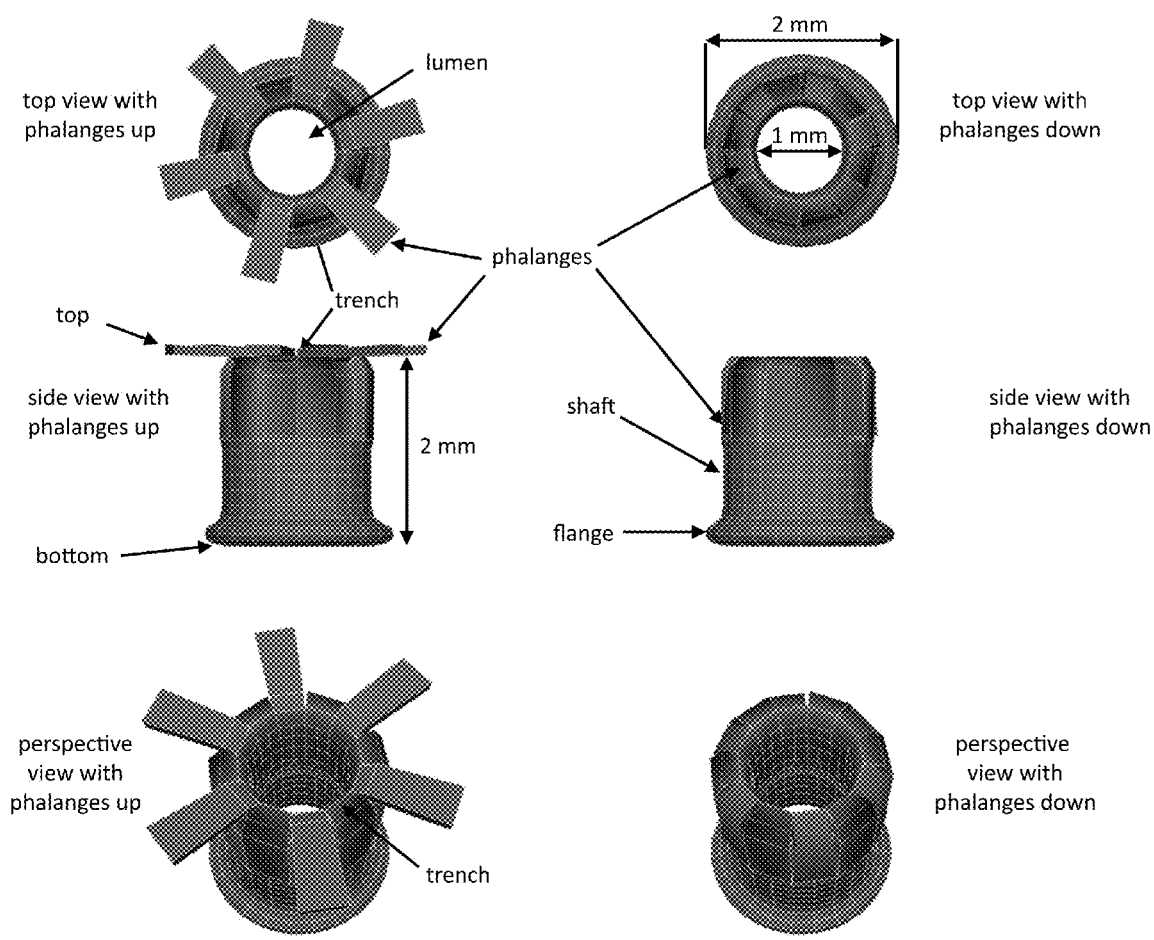

Figure 2. Insertion of a cribriform plate shunt.
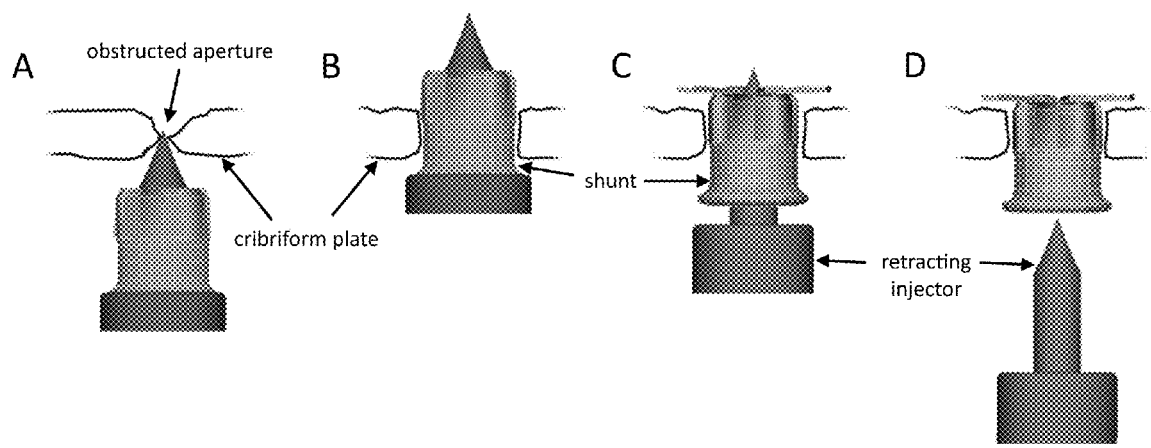

Figure 3. Injector for cribriform plate shunt.
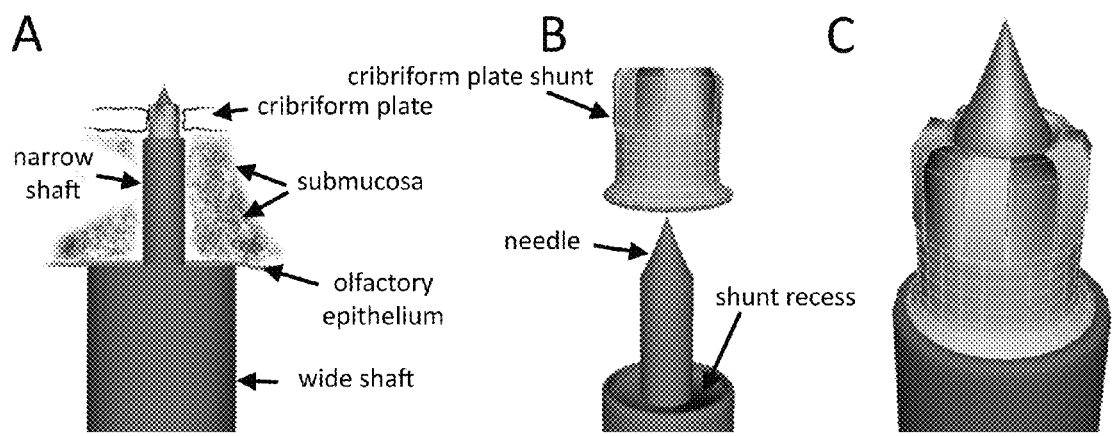

METHOD AND USE OF DRAINING FLUID ABOVE THE CRIBRIFORM PLATE

CROSS-REFERENCE TO RELATED APPLICATIONS

This application claims the benefit of pritority of U.S. Provisional Application No. 61/983,317, filed on Apr. 23, 2014, the content of which is incorporated herein by reference in its entirety.

FIELD OF THE INVENTION

The invention relates to a procedure and devices that facilitate the drainage of fluid from an area overlying the cribriform plate for the purpose of treating neurological and psychiatric disorders, e.g., Alzheimer's disease, Parkinson's disease, Pick's disease, frontal-temporal dementia. In particular, the invention relates a method to insert a shunt that facilitates the regulated flow of fluid from an area overlying the cribriform plate into the nasal submucosa or other body areas. The invention relates to the diagnosis and treatment of neurological disorders associated with reduced drainage of fluid across the cribriform plate, e.g., Alzheimer's disease, Parkinson's disease, Pick's disease, frontal-temporal dementia.

BACKGROUND

Alzheimer's disease is a neurodegenerative brain disorder and a common causes of dementia in the elderly that affected over 5.4 million people in the United States of America in 2013. Since its first description by Alois Alzheimer in 1907 this disease has been thought to result from pathological features in the brain called plaques and tangles. For over one hundred years all clinical efforts to stop or prevent the progression of Alzheimer's disease have failed and new perspectives into the cause(s) of this disorder are lacking. This invention provides a therapeutic approach to treating Alzheimer's disease that emerged from the inventor's understanding that plaques and tangles causative but mere consequences of an underlying mechanism in which the clearance of toxic factors from the brain has been disrupted by genetic and/or environmental factors. A detailed discussion of this reasoning was published after the provisional patent application date and is provided with this application (Ethell, D W; Disruption of cerebrospinal fluid flow through the olfactory system may contribute to Alzheimer's disease pathogenesis, *Journal of Alzheimers Disease* 451(4):1021-30, 2014). Characteristic accumulation of amyloid-beta ($A\beta$) deposits in early Alzheimer's disease indicate the underlying mechanism involves a disruption of interstitial fluid/cerebrospinal fluid (CSF) flow that normally clears debris and toxins from extracellular spaces within the brain. The earliest pathological features of Alzheimer's disease occur in brain areas near the primary olfactory cortex of the brain. During homeostasis, CSF flows from the medial temporal lobe (MTL) along the lateral olfactory stria, through the olfactory trigone and down the olfactory tract to the olfactory bulb, where it seeps through the cribriform plate and into the nasal submucosa. Lymphatic vessels within the nasal submucosa carry off the CSF and metabolites carried therein. The significance of this CSF flow for neurological disease has not been appreciated until this invention, and it is shown here that this pattern of CSF flow clears metabolites, debris and toxins from the hippocampal formation, entorhinal cortex and other structures in the medial temporal lobe, as well as the basal forebrain. Disruption of CSF flow along this route facilitates the accumulation of $A\beta$ in the medial temporal lobe, basal forebrain, and nearby areas, predisposing them to accumulate and trigger the formation of pathological features such as plaques and tangles.

Factors that reduce CSF drainage across the cribriform plate slow the clearance of CSF from the medial temporal lobe and basal forebrain, which can include aging-related bone changes, head trauma, inflammation of the nasal epithelium, toxins that affect olfactory neuron survival and renewal, as well as vascular effects related to diabetes, obesity, and atherosclerosis—all of which have been proposed to affect AD risk; reductions in CSF-mediated clearance also provide links between those life events and familial mutations linked with early onset Alzheimer's disease, in PSEN1, PSEN2, and APP.

Disruption of CSF flow across the cribriform plate predisposes the medial temporal lobe and basal forebrain to pathology, so the intervention attenuates the development of brain pathology by increasing the drainage of CSF from the area overlying the cribriform plate. The invention reduces risks and complications associated with Alzheimer's disease as well as other neurological and psychiatric conditions, e.g., Parkinson's disease, frontal-temporal dementia, mild cognitive impairment, idiopathic dementia, vascular dementia, amyotrophic lateral sclerosis, Pick's disease, concussive brain injury, supranuclear palsy, Creutzfeld-Jacob disease, normal pressure hydrocephalus, multiple sclerosis.

SUMMARY OF THE INVENTION

The invention provides a method to treat neurological disorders and psychiatric conditions by draining CSF from an extracellular compartment above the cribriform plate using shunts.

The invention increases the drainage of CSF from the olfactory bulbs, basal forebrain and medial temporal lobe to treat dementia and other neurological disorders, including Alzheimer's disease, Parkinson's disease, frontal-temporal dementia, mild cognitive impairment, idiopathic dementia, vascular dementia, amyotrophic lateral sclerosis, Pick's disease, concussive brain injury, supranuclear palsy, Creutzfeld-Jacob disease, normal pressure hydrocephalus, multiple sclerosis, as well as other neurological and psychiatric disorders.

The invention can be used to collect CSF from an area overlying the cribriform plate to diagnose and assess neurological disorders, including Alzheimer's disease, Parkinson's disease, frontal-temporal dementia, mild cognitive impairment, idiopathic dementia, vascular dementia, amyotrophic lateral sclerosis, Pick's disease, concussive brain injury, supranuclear palsy, Creutzfeld-Jacob disease, normal pressure hydrocephalus, multiple sclerosis, as well as other neurological and psychiatric disorders.

BRIEF DESCRIPTION OF THE FIGURES

FIG. 1. Design of an internal cribriform plate shunt. Six schematic images of the shunt are shown, two from the top, two from the side and two perspectives. The shunt is made of plastic materials, metal, carbon fibers, or any combination thereof. The central shaft of the example provided is 2 mm with a flange at the bottom; other shaft lengths are also covered. Six flexible phalanges are connected to the top of the shaft such that they are down during insertion, and up when drawn back. Three images of the shunt with phalanges open are shown on the left, and three images of the shunt with phalanges down are shown on the right. The top two images show the shunt from the top and the central lumen is indicated on the left image. When open, the phalanges project above the top of the shaft creating trenches between adjacent phalanges. Examples of some trenches are indicated by arrows on the middle left image (side view with phalanges open) and the bottom left (perspective view with phalanges up).

FIG. 2. Insertion of a cribriform plate shunt illustration. The shunt is mounted on an injector and inserted into an occluded aperture in the cribriform plate (A, B). Above the cribriform plate phalanges of the shunt spread out and lock the shunt in place during retraction of the injector (C). After retraction of the injectors, the shunt is held in position and the lumen allows for drainage of CSF from above the cribriform plate to the nasal submucosa.

FIG. 3. Injector for cribriform plate shunt. The cribriform plate is inserted with an injector. The injector holds the shunt at the end of the narrow shaft on a needle. (A) Schematic of an injector and shunt positioned in the olfactory epithelium, from a side view. Positions of the cribriform plate, submucosa and olfactory epithelium are indicated. The wide shaft rests on the outer olfactory epithelium, is used to gauge insertion depth and prevents over-insertion. (B) Schematic of a close-up view of the needle with a cribriform plate shunt shown above. The shunt recess holds the shunt in place during insertion. (C) Schematic of the tip of an injector mounted with a cribriform plate shunt with phalanges down.

DETAILED DESCRIPTION

Disclosed herein, in certain embodiments, is a method to implant a shunt above or through the cribriform plate to drain fluid from the region immediately above. Fluid draining through the shunt increases the flow of interstitial fluids from contiguous brain areas including but not limited to the olfactory bulbs, the basal forebrain, the olfactory trigone, the anterior temporal lobe, and the medial temporal lobe. It provides a method of treating any patient in need thereof for neurological or psychiatric disease.

In various embodiments, the device and procedure can be used to treat neurological and psychiatric diseases associated with disruptions of cerebrospinal fluid flow and drainage, including Alzheimer's disease, Parkinson's disease, frontal-temporal dementia, mild cognitive impairment, idiopathic dementia, vascular dementia, Pick's disease, concussive brain injury, supranuclear palsy, Creutzfeld-Jacob disease, normal pressure hydrocephalus, multiple sclerosis, as well as other neurological and psychiatric disorders.

In various embodiments, the device and methods can be used to diagnose and assess neurological diseases associated with disruptions of cerebrospinal fluid flow and drainage, including Alzheimer's disease, Parkinson's disease, frontal-temporal dementia, mild cognitive impairment, idiopathic dementia, vascular dementia, Pick's disease, concussive brain injury, supranuclear palsy, Creutzfeld-Jacob disease, normal pressure hydrocephalus, multiple sclerosis, as well as other neurological and psychiatric disorders.

In various embodiments, the device and methods can be used to obtain fluid from above the cribriform plate for the identification or evaluation of infectious agents, metabolic signatures, genetic abnormalities, epigenetic abnormalities, homeostatic and pathological indicators of biological activity, drug efficacy, brain activity.

In various embodiments, the procedure is performed in conjunction with imaging methods to identify and target apertures in the cribriform plate.

In various embodiments drainage can be facilitated by a shunt passing through the cribriform plate and biological membranes attached to that structure, thereby allowing the passage of fluid above the cribriform plate through the shunt and into nasal epithelial tissue below or adjacent to the cribriform plate.

In various embodiments drainage can be facilitated by a tube that runs from an area overlying the cribriform plate to other body cavities including but not limited to the pleural cavity and the peritoneal cavity. The tubing may or may not incorporate mechanisms to regulate flow.

EXAMPLES

A patient with Alzheimer's disease is treated for psychiatric and neurological aspects of the disease by implanting one or several biologically compatible shunts through the cribriform plate as depicted in FIGS. 1-3. The shunt serves as a conduit for CSF to pass from the extracellular compartment surrounding the olfactory bulb into the nasal submucosa. The shunts are inserted nasally using a purpose made device that perforates the cribriform plate and then implants the shunt. In this example the area would be sterilized before procedure. The puncture wound in the overlying nasal epithelium is then sealed with surgical glue any other suitable method.

A patient with Alzheimer's disease is treated for psychiatric and neurological aspects of the disease by implanting biologically compatible tubes to drain fluid from an interstitial compartment immediately above the cribriform plate to the peritoneal cavity. One end of a biologically compatible tube is surgically implanted and affixed to the region above the cribriform plate. The other end of the tube passes through tissues to a subcutaneous area behind the ear. The tube is connected to a flow regulator that is implanted to above or behind the ear. The flow regulator is also connected to an output tube that runs into the peritoneal cavity or pleural cavity. Fluid from the region above the cribriform plate passes through the tube to the regulator then through the second tube to the peritoneal cavity. A port on the regulator allows for the collection of fluid in transit that can be analyzed for diagnostic or therapeutic purposes.

The claimed invention is:

1. A method of draining cerebral spinal fluid in a subject in need thereof, the method comprising perforating the cribriform plate of said subject and draining cerebral spinal fluid from an extracellular compartment above the cribriform plate of said subject.

2. The method of claim 1, wherein said subject has Alzheimer's Disease.

3. The method of claim 1, wherein said perforating is accomplished using a shunt.

* * * * *